(12) United States Patent
Eihusen

(10) Patent No.: US 10,481,133 B2
(45) Date of Patent: Nov. 19, 2019

(54) INLINE CYCLE FUSE

(71) Applicant: Hexagon Technology AS, Alesund (NO)

(72) Inventor: John Eihusen, Lincoln, NE (US)

(73) Assignee: Hexagon Technology, AS, Alesund (NO)

( * ) Notice: Subject to any disclaimer, the term of this patent is extended or adjusted under 35 U.S.C. 154(b) by 241 days.

(21) Appl. No.: 15/613,899

(22) Filed: Jun. 5, 2017

(65) Prior Publication Data

US 2017/0350867 A1    Dec. 7, 2017

Related U.S. Application Data

(60) Provisional application No. 62/346,195, filed on Jun. 6, 2016.

(51) Int. Cl.
  *G01N 9/22*    (2006.01)
  *G01N 29/22*    (2006.01)
  (Continued)

(52) U.S. Cl.
  CPC ........... *G01N 29/227* (2013.01); *F15B 1/083* (2013.01); *F16L 55/07* (2013.01); *F16L 57/00* (2013.01); *F16L 58/00* (2013.01); *G01D 3/08* (2013.01); *G01M 3/007* (2013.01); *G01M 3/04* (2013.01); *G01N 29/14* (2013.01); *G05B 23/0283* (2013.01); *G06Q 10/04* (2013.01); *G06Q 10/20* (2013.01); *F16L 9/18* (2013.01);
  (Continued)

(58) Field of Classification Search
  CPC ........ G01N 29/227; G01D 3/08; F15B 1/083; F16L 55/07; F16L 41/08; F17C 2205/0314

USPC .............................. 73/37, 40.5 R, 49.1, 49.5
See application file for complete search history.

(56) References Cited

U.S. PATENT DOCUMENTS 1,426,956 A    8/1922   Case
1,938,475 A    12/1933  Alexander
(Continued)

FOREIGN PATENT DOCUMENTS

EP        0507673 A1    10/1992
WO   2016001542 A1    1/2016
WO   2017087376 A1    5/2017

OTHER PUBLICATIONS

International Search Report and Written Opinion dated Aug. 7, 2017 for International Application No. PCT/US2017/035942.

*Primary Examiner* — Benjamin R Schmitt
(74) *Attorney, Agent, or Firm* — Mai-Tram D. Lauer; Westman, Champlin & Koehler, P.A.

(57) ABSTRACT

A system and method of predicting impending failure of a pressure vessel include a pressure vessel, a fluid source, a line coupled to the pressure vessel and to the fluid source, an apparatus, a sensor and a controller. The apparatus includes a conduit and a containment structure. The containment structure includes a cavity separated from an interior of the conduit by a portion of a conduit wall of the conduit. The sensor is configured to determine a value of a physical property in the cavity. The controller is in signal communication with the sensor and configured to detect a change in the value. The method includes determining a first value of a physical property in the cavity, experiencing a failure of the conduit wall, determining a second value of the physical property in the cavity, and detecting a difference between the first and second values.

6 Claims, 5 Drawing Sheets

(51) Int. Cl.
  *G01D 3/08*   (2006.01)
  *G01N 29/14*  (2006.01)
  *G05B 23/02*  (2006.01)
  *G06Q 10/04*  (2012.01)
  *G06Q 10/00*  (2012.01)
  *F16L 57/00*  (2006.01)
  *F16L 58/00*  (2006.01)
  *F15B 1/08*   (2006.01)
  *F16L 55/07*  (2006.01)
  *G01M 3/00*   (2006.01)
  *G01M 3/04*   (2006.01)
  *F16L 9/18*   (2006.01)
  *F16L 39/00*  (2006.01)
  *F16L 41/02*  (2006.01)

(52) U.S. Cl.
  CPC ............ *F16L 39/00* (2013.01); *F16L 41/021* (2013.01); *F16L 2201/30* (2013.01); *F17C 2205/0314* (2013.01); *F17C 2260/036* (2013.01); *F17C 2260/038* (2013.01)

(56) References Cited

U.S. PATENT DOCUMENTS

| | | |
|---|---|---|
| 1,962,168 A | 6/1934 | Andrus |
| 1,975,832 A | 10/1934 | Florez |
| 1,977,177 A | 10/1934 | Florez |
| 2,233,403 A | 3/1941 | Dickinson |
| 2,726,683 A | 12/1955 | Steinbach |
| 2,937,520 A * | 5/1960 | Bell ............ F16L 23/167 73/40.5 R |
| 3,922,999 A | 12/1975 | Meginnis |
| 4,448,062 A | 5/1984 | Peterson |
| 4,617,822 A | 10/1986 | Davis |
| 4,642,557 A | 2/1987 | Ross |
| 4,779,453 A | 10/1988 | Hopenfeld |
| 4,922,748 A | 5/1990 | Hopenfeld |
| 5,024,755 A | 6/1991 | Livsey |
| 5,659,128 A | 8/1997 | Goldenberg |
| 6,006,588 A | 12/1999 | Cartwright |
| 6,080,982 A | 6/2000 | Cohen |
| 6,131,443 A | 10/2000 | Duncan |
| 6,945,098 B2 | 9/2005 | Olson |
| 8,602,065 B2 | 12/2013 | Aulanko |

* cited by examiner

INLINE CYCLE FUSE

CROSS-REFERENCE TO RELATED APPLICATION

This application claims the benefit of priority of U.S. Provisional Patent Application No. 62/346,195, filed Jun. 6, 2016, to an "Inline Cycle Fuse," which is hereby incorporated by reference in its entirety.

BACKGROUND

Pressure vessels are commonly used for containing a variety of gases or fluids under pressure, such as hydrogen, oxygen, natural gas, nitrogen, propane and other fuels, for example. Generally, pressure vessels can be of any size or configuration. The vessels can be heavy or light, single-use (e.g., disposable), reusable, subjected to high pressures (greater than 50 psi, for example), low pressures (less than 50 psi, for example), or used for storing fluids at elevated or cryogenic temperatures, for example.

Suitable pressure vessel shell materials include metals, such as steel; or composites, which may be formed of laminated layers of wound fiberglass filaments or other synthetic filaments bonded together by a thermo-setting or thermoplastic resin. A liner or bladder is often disposed within a pressure vessel shell to seal the vessel, thereby serving as a fluid permeation barrier.

Generally, pressure vessels have limited lifetimes, and it is desirable to remove a pressure vessel from service before it fails, as failures can be catastrophic and cause damage or injury. Both cyclic fatigue and static fatigue (stress rupture) contribute to the fatigue load, and thus the failure, of pressure vessels. The calendar life of a pressure vessel, or the number of fatigue cycles over a specific pressure range (for example, from near empty to full), is commonly used to determine when to remove a vessel from service. However, in some applications, the pressure ranges and number of cycles applied to the pressure vessel are inconsistent and/or unknown. In addition, the interaction between cyclic fatigue life and static fatigue life is not well understood. The effects of cycling combine in unknown ways with the effects of the duration the pressure vessel spends at full pressure without cycling.

Mathematical projections of vessel lifetime are commonly used to evaluate the fatigue life of a pressure vessel. This requires that the number of cycles be counted or estimated, then sorted by mean stress levels and stress range. These cycles are combined into an equivalent number of full-range cycles to estimate the remaining vessel life. It must then be determined how to combine this information with static fatigue. Uncertainties are inherent in the calculation and estimation of cycles, in combining cycle effects, and in assessing the total and remaining life of the pressure vessel.

SUMMARY

In one aspect, this disclosure describes a system including a pressure vessel, a fluid source, a line coupled to the pressure vessel and to the fluid source, an apparatus, a sensor and a controller. The apparatus includes a conduit and a containment structure. The conduit has a conduit wall, wherein the conduit is configured for fluid connection to the line. The containment structure includes a cavity separated from an interior of the conduit by a portion of the conduit wall. The sensor is configured to determine a value of a physical property in the cavity. The controller is in signal communication with the sensor and configured to detect a change in the value.

In another aspect, this disclosure describes a method of predicting impending failure of a pressure vessel. The method includes fluidly connecting the pressure vessel to a source of pressurized fluid via a line and fluidly connecting an apparatus to the line between the pressure vessel and the source. The apparatus includes a conduit and a containment structure. The conduit has a conduit wall, wherein the conduit is configured for fluid connection to the line. The containment structure includes a cavity separated from an interior of the conduit by a portion of the conduit wall. The method further includes determining a first value of a physical property in the cavity of the containment structure, experiencing a failure of the conduit wall that permits the fluid to flow from the interior of the conduit into the cavity, determining a second value of the physical property in the cavity, and detecting a difference between the first and second values.

This disclosure, in its various combinations, either in apparatus or method form, may also be characterized by the following listing of items:

1. A system including:
    a pressure vessel;
    a fluid source;
    a line coupled to the pressure vessel and to the fluid source;
    an apparatus including:
        a conduit having a conduit wall, wherein the conduit is configured for fluid connection to the line; and
        a containment structure including a cavity separated from an interior of the conduit by a portion of the conduit wall;
    a sensor configured to determine a value of a physical property in the cavity; and
    a controller in signal communication with the sensor and configured to detect a change in the value.
2. The system of item 1 wherein the physical property is selected from the group consisting of pressure, temperature, acoustic emission, conductivity, resistance, capacitance, optical, and substance concentration.
3. The system of any of items 1-2 further including an indicator in signal communication with the controller.
4. The system of any of items 1-3 further including a valve disposed between the fluid source and the pressure vessel.
5. The system of item 4, wherein the valve is in signal communication with the controller.
6. The system of any of items 1-5 further including a weakness located on the portion of the conduit wall and configured such that the conduit wall fails at the weakness to permit the fluid to flow from the interior of the conduit into the cavity of the containment structure.
7. A method of predicting impending failure of a pressure vessel, the method including:
    fluidly connecting the pressure vessel to a source of pressurized fluid via a line;
    fluidly connecting an apparatus to the line between the pressure vessel and the source, the apparatus including:
        a conduit having a conduit wall, wherein the conduit is configured for fluid connection to the line; and
        a containment structure including a cavity separated from an interior of the conduit by a portion of the conduit wall;
    determining a first value of a physical property in the cavity of the containment structure;

experiencing a failure of the conduit wall that permits the fluid to flow from the interior of the conduit into the cavity;

determining a second value of the physical property in the cavity; and detecting a difference between the first and second values.

8. The method of item 7 further including determining whether the difference exceeds a pre-determined threshold difference.

9. The method of item 8 further including:

determining that the difference exceeds a pre-determined threshold difference; and relaying a signaling to a user.

10. The method of any of items 8-9 further including:

determining that the difference exceeds a pre-determined threshold difference; and closing a valve between the source and the pressure vessel.

11. The method of item 10 wherein closing the valve is accomplished automatically by a controller.

12. The method of any of items 7-11 wherein the physical property is selected from the group consisting of pressure, temperature, acoustic emission, conductivity, resistance, capacitance, optical, and substance concentration.

13. The method of any of items 7-12 further including calibrating the failure of the conduit wall to occur at a pre-determined percentage of an estimated useful life of the pressure vessel.

This summary is provided to introduce concepts in simplified form that are further described below in the Detailed Description. This summary is not intended to identify key features or essential features of the disclosed or claimed subject matter and is not intended to describe each disclosed embodiment or every implementation of the disclosed or claimed subject matter. Specifically, features disclosed herein with respect to one embodiment may be equally applicable to another. Further, this summary is not intended to be used as an aid in determining the scope of the claimed subject matter. Many other novel advantages, features, and relationships will become apparent as this description proceeds. The figures and the description that follow more particularly exemplify illustrative embodiments.

BRIEF DESCRIPTION OF THE DRAWINGS

The disclosed subject matter will be further explained with reference to the attached figures, wherein like structure or system elements are referred to by like reference numerals throughout the several views.

While the above-identified figures set forth one or more embodiments of the disclosed subject matter, other embodiments are also contemplated, as noted in the disclosure. In all cases, this disclosure presents the disclosed subject matter by way of representation and not limitation. It should be understood that numerous other modifications and embodiments can be devised by those skilled in the art which fall within the scope and spirit of the principles of this disclosure.

The figures may not be drawn to scale. In particular, some features may be enlarged relative to other features for clarity. Moreover, where terms such as above, below, over, under, top, bottom, side, right, left, etc., are used, it is to be understood that they are used only for ease of understanding the description. It is contemplated that structures may be oriented otherwise.

DETAILED DESCRIPTION

The disclosure recognizes that it is desirable to anticipate vessel failure, allowing preemptive removal of a vessel from service before it fails. In an exemplary embodiment, a fuse is positioned in-line with a fluid flow, for instance, along a flow line into or out of a pressure vessel. The fuse is constructed to safely indicate a maximum-allowed cycle load. In one embodiment, a fuse includes a containment cavity and a small conduit that is scored or machined to have a weakness such as a notch- or divot-like flaw in the portion of the conduit that runs through the containment cavity. In another embodiment, a fuse includes a conduit that is formed with a material and/or structure designed to fail before expected failure of a connected pressure vessel. Fluid flows into and out of the pressure vessel through the conduit. After exposure to a maximum-allowed cycle load, stresses due to pressure cycling cause the conduit to fail, such as at the location of the flaw. When the conduit is breached, it vents into the containment cavity until a physical property such as the internal pressure of the cavity matches that of the conduit. The increased pressure in the cavity may be used to trigger alarms indicating that the maximum cycle load has been reached. Further, the leak may be safely routed to a vent system. Accordingly, the disclosed systems and methods allow a user to predict impending failure of a connected pressure vessel. In an exemplary embodiment, the fuse is calibrated to fail at a predetermined percentage of a pressure vessel's estimated useful life.

Figure 1:
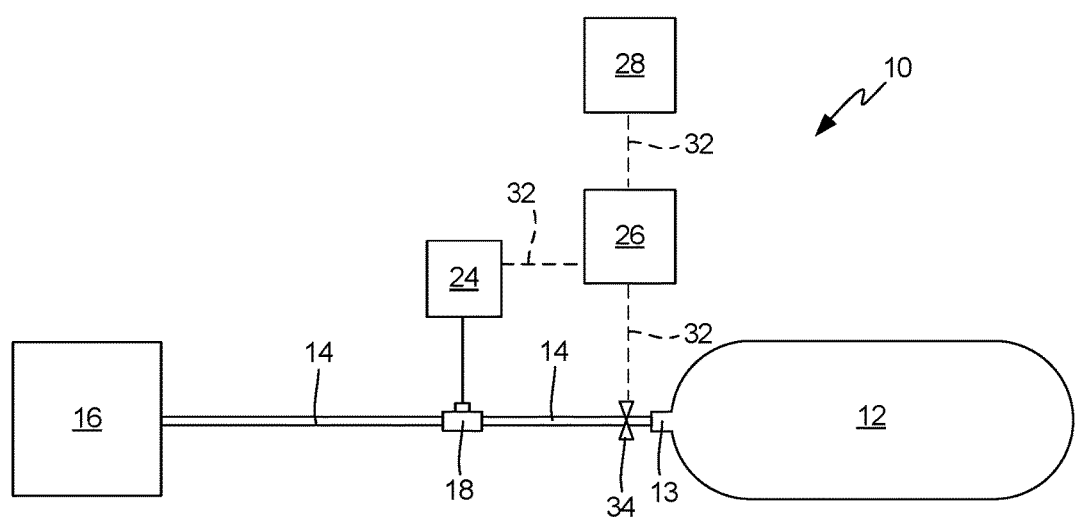
FIG. 1 shows a schematic view of an exemplary system including a pressure vessel and an exemplary fuse coupled in series to a fluid source.

FIG. 1 shows a schematic illustration of an exemplary embodiment of a pressure vessel failure indicator system 10, which includes pressure vessel 12 coupled (e.g., in fluid communication) to a conduit such as source line 14. Source line 14 may be, for example, metallic and/or polymer conduit or tubing. Pressure vessel 12 is configured to contain a liquid or gaseous fluid under pressure and include metallic and/or composite construction. Suitable metals include, for example, stainless steel and nickel alloys. Suitable composite materials include, for example, fiberglass or carbon fiber. Source line 14 allows fluidic communication of pressure vessel 12 with a source of pressurized fluid 16, which provides the fluid with which pressure vessel 12 is filled. Valve 34 is disposed on source line 14 between fluid source 16 and pressure vessel 12. When valve 34 is open, pressure vessel 12 and fluid source 16 are in fluid communication. Conversely, when valve 34 is closed, no flow occurs between fluid source 16 and pressure vessel 12.

In the illustrated embodiment, the fuse 18 is disposed in series with pressure vessel 12 with respect to the source 16. However, other arrangements may also be suitable. Typically, pressure vessel 12 is coupled to line 14 via boss 13 of pressure vessel 12, but any coupling mechanism that allows fluid in line 14 to selectively flow into and out of pressure vessel 12 may be used. Details relevant to the formation of an exemplary pressure vessel 12 are disclosed in U.S. Pat. No. 4,838,971, entitled "Filament Winding Process and Apparatus;" and U.S. Pat. No. 4,369,894, entitled "Filament Wound Vessels;" both of which are incorporated herein by reference.

In an exemplary embodiment of system 10, an apparatus such as fuse 18 may be designed to have a predetermined time-to-failure (e.g., life expectancy duration) that is less than the expected time-to-failure of pressure vessel 12 by an amount that allows fuse 18 to signal an impending failure of pressure vessel 12. The expected life duration of pressure vessel 12 may be defined by a number of pressure cycles and/or a time duration at one or more static pressures, for example, before structural integrity of pressure vessel 18 is compromised enough to cause failure.

Figure 3:
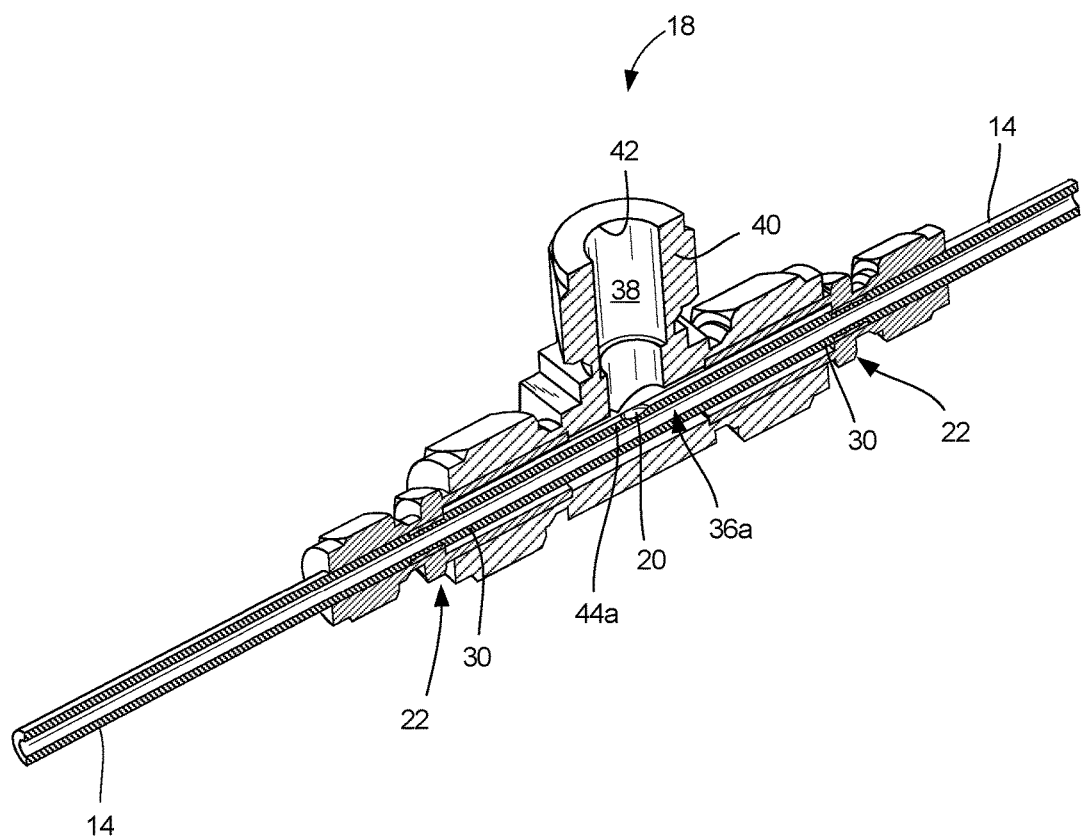
FIG. 3 is a perspective cross-sectional view of the fuse taken along line 3-3 of FIG. 2

As shown in FIG. 3, an exemplary embodiment of fuse 18 includes conduit 36a configured for fluid connection to conduit 14 such that fluid flowing through conduit 14 also flows through conduit 36a. While conduit 36 is illustrated as a cylindrical conduit in FIGS. 3-5, it is contemplated that other pipe forms and shapes may also be used. In an exemplary embodiment, conduit 36a has a conduit wall 44a. At least one weakness 20, such as a notch or divot, may be located on conduit wall 44a. Thus, mechanical failure initiates at weakness 20 before occurring at another location on fuse 18. In an exemplary embodiment, weakness 20 is scored or machined into conduit 36 at a precise depth in a metallic conduit wall 44. Weakness 20 is calibrated so that conduit wall 44a breaks before pressure vessel 12 fails, such as at a pre-determined percentage of the pressure vessel's estimated useful life. It is contemplated that any weakness 20 may be employed, such as, for example, an area of conduit wall 44a having a different thickness, composition, structure, susceptibility to corrosion, or other property, rendering the weakness more susceptible to failure than a remainder of fuse 18.

One or more sensors 24 may be located in, on, or connected to fuse 18 and be configured to detect one or more conditions of fuse 18. For example, sensor 24 may be configured to detect one or more physical conditions in fuse 18, such as temperature, pressure, acoustic emissions, conductivity, or any other indicator of failure of conduit wall 44, such as at weakness 20. Sensor 24 may be connected to controller 26 via signal communication line 32.

For ease of discussion, reference will be made to computer controller 26, which can include known processors, microprocessors, microcontrollers, and programmable logic controllers (PLC), for example. In an exemplary embodiment, controller 26 runs software and thereby communicates with external devices, such as sensor 24, indicator 28, valve 34 and any other external devices, via signal communication lines 32. In an exemplary embodiment, such signal communication can be performed via interfaces (not shown), such as one using a standard RS-485/Modbus protocol, using hard wired and/or wireless communication means.

Controller 26 receives a signal from a sensor 24 regarding one or more sensed values of a physical condition and runs software (not shown) to determine whether failure of conduit 36 has occurred, as a function of the sensed value(s). In an exemplary embodiment, one or both of indicator 28 and valve 34 are in signal communication with controller 26 via signal communication lines 32. Controller 26 is configured to respond to a failure of source line 14, for example, by triggering indicator 28 to relay a signal to a user and/or removing pressure vessel 12 from service. In one example, triggering indicator 28 includes sending a signal from controller 26 to actuate a visible and/or audible signal or alarm to users of breach of source line 14 at conduit 36. In another example, removing pressure vessel 12 from service includes disconnecting pressure vessel 12 from fluid source 16, such as by sending a signal from controller 26 to automatically close valve 34 between pressure vessel 12 and fluid source 16, thereby stopping fluid flow between fluid source 16 and pressure vessel 12. In addition or alternatively, pressure vessel 12 may be manually dismounted or otherwise removed from service, either before or after an alert of failure, for inspection.

Figure 2:
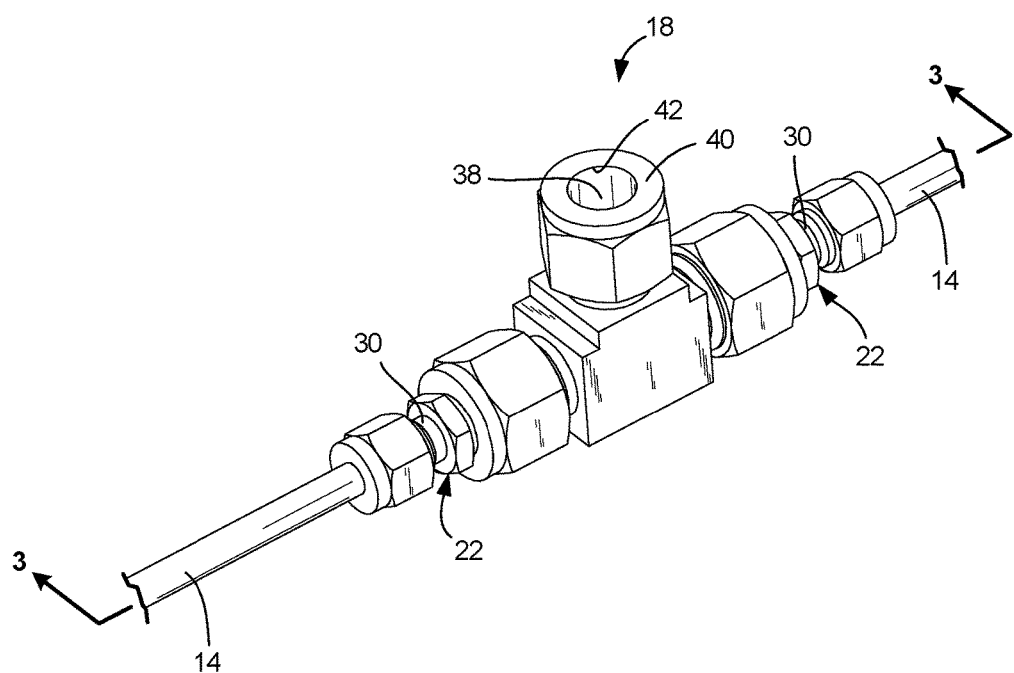
FIG. 2 is a perspective view of an exemplary fuse.

Referring to FIGS. 2 and 3, in some embodiments, fuse 18 is formed integrally with source line 14. In other embodiments, fuse 18 is formed as a separate component that can be connected to segments of source line 14, such as at fasteners 22, which include nuts and washers threadably attached to shaft 30 in an exemplary embodiment. As shown in FIG. 3, in an exemplary embodiment, fuse 18 includes conduit 36a having weakness 20 formed on conduit wall 44a. Gas flowing through source line 14 also flows through conduit 36. The configuration of weakness 20 and the material of conduit 36a are calibrated so that conduit 36a breaks at weakness 20 at a pre-determined pressure cycle load passing through source line 14, wherein such a pre-determined pressure cycle load is calculated to be reflective of an expected life duration of pressure vessel 12 attached to source line 14. Upon failure of conduit 36a at weakness 20, the gas flowing in source line 14 escapes from an interior of conduit 36a into cavity 38 of containment structure 40. As shown in FIGS. 1 and 2, sensor 24 is connected to cavity 38 of fuse 18, such as via a connection at aperture 42, to sense one or more values of physical conditions in cavity 38. While a particular configuration of containment structure 40 is illustrated, it is contemplated that containment structure 40 may differ in size and shape from the illustrated embodiment. However, whatever the configuration of containment structure 40, fluid communication between source line 14 and cavity 38 is provided by the rupture of conduit 36a, such as at weakness 20. While it appears in FIGS. 2 and 3 that containment structure 40 is open at aperture 42, in an exemplary embodiment, sensor 24 is attached to fuse 18 at aperture 42, such as by a coupler or other known connection.

In an exemplary embodiment, "failure" of conduit 36 includes rupture thereof or a smaller breach that results in fluid leakage therefrom of a larger than threshold amount. Such a threshold amount may be set by a user and/or determined by software run by controller 26 that takes into account factors including, for example, the sensed physical conditions whose values are determined by one or more sensors 24. Sensor 24 is configured to determine a value of a physical property in cavity 38. Exemplary values of physical properties include, for example, a temperature reading, a pressure value, a conductivity value, an acoustic emission wavelength or frequency, and electrical capacitance or resistance value, an optical value, and a substance concentration percentage. Controller 26 is in signal communication with sensor 24 via signal communication line 32. Controller 26 receives multiple readings from sensor 24, such as at timed intervals, for example, and is configured to detect a change in the values detected by sensor 24.

In one example, the pressurized fluid in system 10 is a cryogenic fluid. Sensor 24 returns a first temperature value of the cavity 38 and a second temperature value of the cavity 38. Controller 26 calculates a difference between the first and second values. Controller 26 may run software or otherwise be programmed to determine that rupture of the conduit wall 44 at weakness 20 has occurred if the difference is above a pre-determined threshold difference. In another method, even more simply, controller 26 may determine that failure at fuse 18 has occurred if any of the sensed temperature values is below or above pre-determined one or more threshold temperature values.

In another example, if the pressurized fluid in system 10 is hydrogen, controller 26 may determine that failure of source line 14 has occurred if sensor 24 returns a concentration value of hydrogen in the cavity 38 of containment structure 40 that is above a pre-determined threshold hydrogen concentration, or that a difference in substance concentration values exceeds a pre-determined threshold difference. In yet another example, controller 26 may determine that failure of source line 14 has occurred if sensor 24 returns a pressure value of gas in the cavity 38 of containment structure 40 that is above a pre-determined threshold pressure, or that a difference in measured pressure values exceeds a pre-determined threshold difference. Software run by controller 26 may also be programmed to take into consideration any combination of physical condition values returned by sensors 24 to determine whether failure of source line 14 has occurred.

Figure 4:
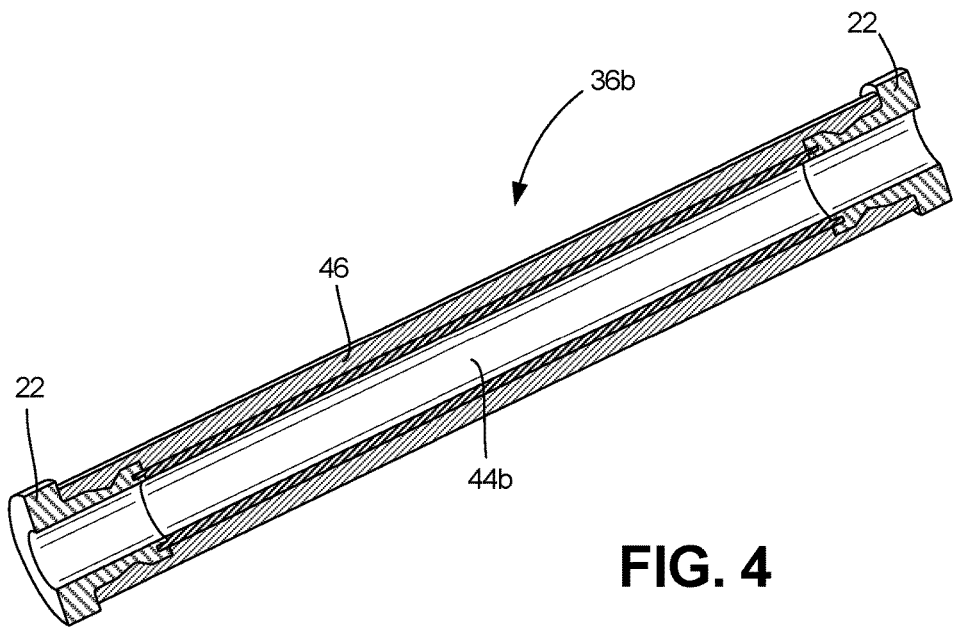
FIG. 4 is a perspective cross-sectional view of a second exemplary embodiment of a conduit of a fuse of the present disclosure.
Figure 5:
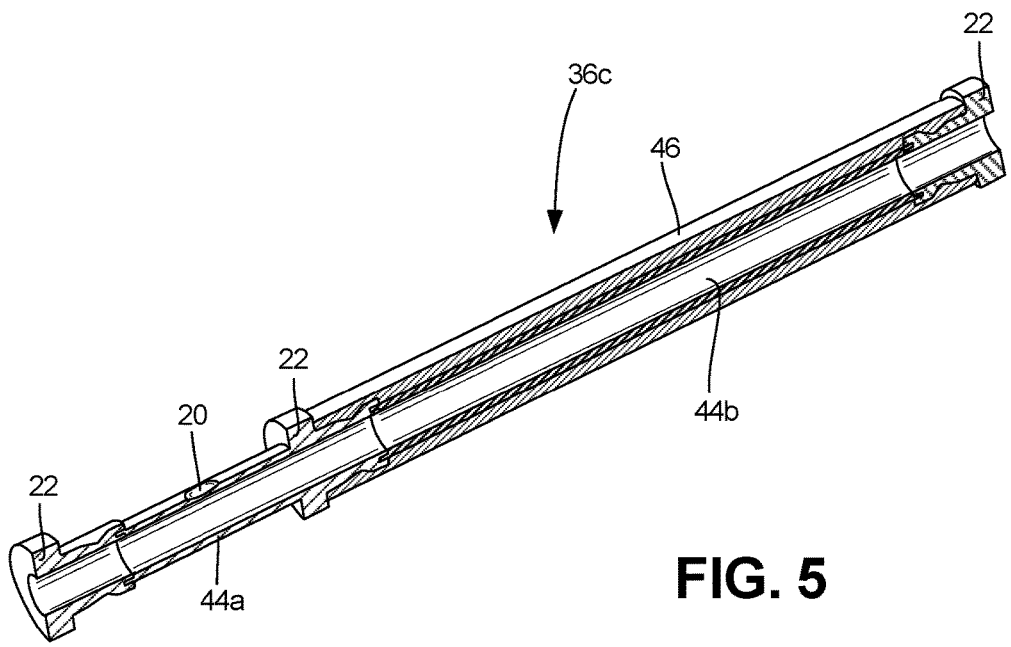
FIG. 5 is a perspective cross-sectional view of a third exemplary embodiment of a conduit usable in the disclosed fuse.
Figure 6:
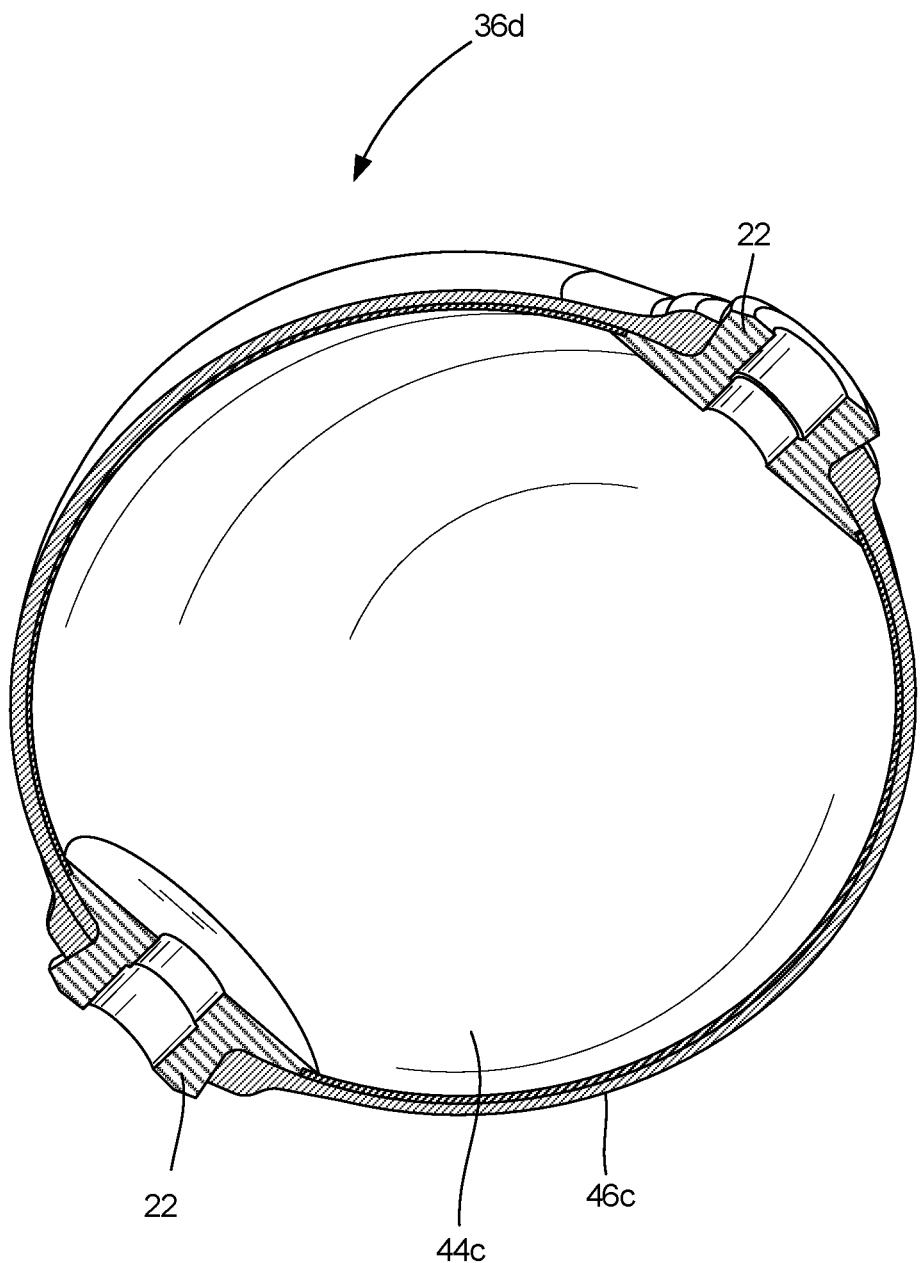
FIG. 6 is a perspective cross-sectional view of a fourth exemplary embodiment of a conduit for use in the disclosed fuse.

FIGS. 4-6 illustrate exemplary embodiments of other configurations of conduits 36 that can be used in fuse 18. As shown in FIG. 4, in an exemplary embodiment, conduit 36b includes a conduit wall 44b that may be formed of a material such as a polymer. Overwrap layer 46 formed surrounding conduit wall 44b may be formed as a filament-wound composite material, which may be similar in composition and construction to a composite shell material of the protected pressure vessel 12. The overwrap layer 46 is configured in its composition and/or structure to fail before an expected failure of the pressure vessel 12. Unlike conduit 36a of FIG. 3, conduit 36b of FIG. 4 does not have a discrete point of weakness, but rather could fail at any point along conduit wall 44b and/or overwrap layer 46. Accordingly, a containment structure 40 for use with conduit 36b may include a larger cavity 38 that envelops all portions of conduit 36b between fasteners 22. A conduit 36b as shown in FIG. 4 may be most useful for predicting a static fatigue limit on the composite shell of pressure vessel 12. In contrast, conduit 36a of FIG. 3, having a discrete machined weakness 20 on a conduit wall 44a, may be most useful for predicting failure with respect to a predetermined number of pressurization cycles.

Conduit 36c of FIG. 5 combines the features of conduit 36a of FIG. 3 and conduit 36b of FIG. 4. A containment structure 40 for use with conduit 36b would, in an exemplary embodiment, include a cavity 38a that encompasses the entire conduit 36c between the outer fasteners 22. It is expected that in use, conduit wall 44b would be breached when a static fatigue limit of overwrap layer 46 is reached, which is calibrated to be before a point of failure of a composite shell of pressure vessel 12. Moreover, it is expected that conduit wall 44a would be breached at weakness 20 when a set number of cycles of pressurization have been experience at conduit wall 44a. Thus, the combination conduit 36c is effective to protect the pressure vessel 12 against expected static fatigue and pressurization cycle limits.

As shown in FIG. 6, conduit 36d is similar in composition as conduit 36b of FIG. 4. However, the structural shape of conduit wall 44c and overwrap layer 46c are not limited to the tubular structures shown in FIGS. 3-5. Rather, as shown in FIG. 6, a conduit 36d can have a spherical geometry. Moreover, it is contemplated that conduits 36 having yet other geometrical configurations may be suitable and the present disclosure is not limited to the particularly illustrated embodiments. Moreover, as with FIG. 5, the conduit 36d of FIG. 6 can also be combined with a pressure cycle predictive device similar to conduit wall 44a with weakness 20 formed therein. As with the other discussed embodiments, it is contemplated that a containment structure 40 would surround conduit 36d and could be outfitted with other components such as sensor 24, controller 26, indicator 28 and signal communication line 32 as discussed above.

In some embodiments, the geometry of a conduit 36 can be used to generate stress failure locations in the conduit wall 44c and/or the overwrap layer 46c that perform similarly to the weakness 20 of conduit wall 44a.

While the disclosed fuses 18 having different conduits 36 have been described as being including a containment structure 40 configured to operate as described with reference to failure indicator system 10 of FIG. 1, it is also contemplated that the disclosed conduits 36 could additionally or alternatively be placed in fluid communication with a venting system. Such a venting system could safely and controllably release the pressurized fluid from a pressure vessel 12 and/or fluid source 16 to prevent an uncontrolled release of fluid or rupture of the pressure vessel.

Although the subject of this disclosure has been described with reference to several embodiments, workers skilled in the art will recognize that changes may be made in form and detail without departing from the scope of the disclosure. In addition, any feature disclosed with respect to one embodiment may be incorporated in another embodiment, and vice-versa.

What is claimed is:

1. A method of predicting impending failure of a pressure vessel, the method including:
    fluidly connecting the pressure vessel to a source of pressurized fluid via a line;
    fluidly connecting an apparatus to the line between the pressure vessel and the source, the apparatus including:
        a conduit having a conduit wall, wherein the conduit is configured for fluid connection to the line; and
        a containment structure including a cavity separated from an interior of the conduit by a portion of the conduit wall;
    determining a first value of a physical property in the cavity of the containment structure;
    experiencing a failure of the conduit wall that permits the fluid to flow from the interior of the conduit into the cavity;
    determining a second value of the physical property in the cavity;
    detecting a difference between the first and second values; and
    calibrating the failure of the conduit wall to occur at a pre-determined percentage of an estimated useful life of the pressure vessel.

2. The method of claim 1 further including determining whether the difference exceeds a pre-determined threshold difference.

3. The method of claim 2 further including:
    determining that the difference exceeds a pre-determined threshold difference; and
    relaying a signaling to a user.

4. The method of claim 2 further including:
    determining that the difference exceeds a pre-determined threshold difference; and
    closing a valve between the source and the pressure vessel.

5. The method of claim 4 wherein closing the valve is accomplished automatically by a controller.

6. The method of claim 1 wherein the physical property is selected from the group consisting of pressure, temperature, acoustic emission, conductivity, resistance, capacitance, optical, and substance concentration.

\* \* \* \* \*